United States Patent
Kusters et al.

(10) Patent No.: US 9,440,396 B2
(45) Date of Patent: Sep. 13, 2016

(54) STERILE CONNECTION DEVICE FOR MAKING MULTIPLE CONNECTIONS

(71) Applicant: Fenwal, Inc., Lake Zurich, IL (US)

(72) Inventors: Benjamin E. Kusters, Pleasant Prairie, WI (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 208 days.

(21) Appl. No.: 14/309,305

(22) Filed: Jun. 19, 2014

(65) Prior Publication Data

US 2015/0367569 A1 Dec. 24, 2015

(51) Int. Cl.
*B29C 65/04* (2006.01)
*B29C 65/78* (2006.01)
*A61M 39/14* (2006.01)
(Continued)

(52) U.S. Cl.
CPC ............ *B29C 66/857* (2013.01); *A61M 39/14* (2013.01); *A61M 39/146* (2013.01); *A61M 39/18* (2013.01); *B29C 65/04* (2013.01); *B29C 65/203* (2013.01); *B29C 65/2046* (2013.01); *B29C 65/743* (2013.01); *B29C 65/7802* (2013.01); *B29C 65/7841* (2013.01); *B29C 66/02241* (2013.01); *B29C 66/1142* (2013.01); *B29C 66/5221* (2013.01); *B29C 66/7373* (2013.01); *B29C 66/73921* (2013.01); *B29C 66/81431* (2013.01); *B29C 66/81871* (2013.01); *B29C 66/8221* (2013.01); *B29C 66/8324* (2013.01); *B29C 66/71* (2013.01); *B29L 2023/007* (2013.01); *Y10T 156/1751* (2015.01)

(58) Field of Classification Search
CPC . B29C 65/04; B29C 65/743; B29C 65/7802; B29C 65/7841; B29C 66/0224; B29C 66/02241; B29C 66/1142; B29C 66/5221; B29C 66/7373; B29C 66/73921; B29C 66/81431; B29C 66/81871; B29C 66/8221; B29C 66/83221; B29C 66/8324; B29C 66/857; A61M 39/146; B29L 2023/007
See application file for complete search history.

(56) References Cited

U.S. PATENT DOCUMENTS 3,968,195 A 7/1976 Bishop
4,030,494 A 6/1977 Tenczar
(Continued)

FOREIGN PATENT DOCUMENTS

EP 0134630 B 5/1989
EP 0194873 B1 7/1991
(Continued)

OTHER PUBLICATIONS

Notification of Transmittal of the International Search Report, International Search Report and Written Opinion for PCT/US2012/069103 dated Feb. 28, 2013.
(Continued)

*Primary Examiner* — Michael Tolin
(74) *Attorney, Agent, or Firm* — Cook Alex Ltd.

(57) ABSTRACT

System, method and apparatus for making a plurality of sterile connections between a plurality of pairs of thermoplastic tubes. A first receiver receives a first tube, a second receiver receives second and third tubes, and a third receiver receives a fourth tube. The first and second receivers are movable to place clamped and heated ends of first and second tubes into contact and the second and third receivers are movable to place clamped and heated ends of third and fourth tubes into contact.

28 Claims, 9 Drawing Sheets

(51) Int. Cl.
  B29C 65/00    (2006.01)
  A61M 39/18   (2006.01)
  B29C 65/20    (2006.01)
  B29C 65/74    (2006.01)
  B29L 23/00    (2006.01)

(56) References Cited

U.S. PATENT DOCUMENTS

| | | |
|---|---|---|
| 4,157,723 A | 6/1979 | Granzow et al. |
| 4,369,779 A | 1/1983 | Spencer |
| 4,412,835 A | 11/1983 | Spencer |
| 4,443,215 A | 4/1984 | Smith |
| RE32,056 E | 12/1985 | Granzow et al. |
| 4,596,551 A | 6/1986 | Golinski et al. |
| 4,619,642 A | 10/1986 | Spencer |
| 4,673,400 A | 6/1987 | Martin |
| 4,737,214 A | 4/1988 | Leurink et al. |
| 4,753,697 A | 6/1988 | Shaposka et al. |
| 4,770,735 A | 9/1988 | Shaposka et al. |
| 4,793,880 A | 12/1988 | Shaposka et al. |
| 4,828,557 A | 5/1989 | Persidsky |
| 4,832,773 A | 5/1989 | Shaposka et al. |
| 4,864,101 A | 9/1989 | Shaposka et al. |
| 4,897,138 A | 1/1990 | Shaposka et al. |
| 4,913,756 A | 4/1990 | Shaposka et al. |
| 4,933,036 A | 6/1990 | Shaposka et al. |
| 5,009,645 A | 4/1991 | Silver et al. |
| 5,141,592 A | 8/1992 | Shaposka et al. |
| 5,156,701 A | 10/1992 | Spencer et al. |
| 5,158,630 A | 10/1992 | Shaposka et al. |
| 5,182,440 A | 1/1993 | Dufour et al. |
| 5,209,800 A | 5/1993 | Spencer et al. |
| 5,244,522 A | 9/1993 | Spencer et al. |
| 5,248,359 A | 9/1993 | Shaposka et al. |
| 5,256,229 A | 10/1993 | Spencer |
| 5,256,845 A | 10/1993 | Schippers |
| 5,272,304 A | 12/1993 | Been et al. |
| 5,279,685 A | 1/1994 | Ivansons et al. |
| 5,342,345 A | 8/1994 | Spencer |
| D355,848 S | 2/1995 | Ivansons et al. |
| 5,397,425 A | 3/1995 | Ivansons et al. |
| D357,926 S | 5/1995 | Ivansons et al. |
| 5,518,575 A | 5/1996 | Watanabe |
| 5,525,186 A | 6/1996 | Ivansons et al. |
| 5,632,852 A | 5/1997 | Ivansons et al. |
| 5,674,333 A | 10/1997 | Spencer |
| 5,733,268 A | 3/1998 | Spencer |
| 5,802,689 A | 9/1998 | Sano |
| 5,855,731 A | 1/1999 | Spencer |
| 5,858,016 A | 1/1999 | Bacehowski et al. |
| 5,871,612 A | 2/1999 | Spencer |
| 5,919,173 A | 7/1999 | Spencer |
| 5,928,216 A | 7/1999 | Spencer |
| 6,020,574 A | 2/2000 | Ivansons |
| 6,026,882 A | 2/2000 | Yamada et al. |
| 6,071,690 A | 6/2000 | Spencer |
| 6,132,833 A | 10/2000 | Spencer |
| 6,177,652 B1 | 1/2001 | Ivansons |
| 6,341,637 B1 | 1/2002 | Yamada et al. |
| 6,348,049 B1 | 2/2002 | Spencer |
| 6,416,489 B1 | 7/2002 | Booth |
| 6,460,592 B1 | 10/2002 | Sano et al. |
| 6,463,979 B1 | 10/2002 | Sano et al. |
| 6,485,593 B1 | 11/2002 | Christoffersen |
| 6,596,122 B1 | 7/2003 | Savitski et al. |
| 6,637,489 B1 | 10/2003 | Spencer |
| 6,705,372 B2 | 3/2004 | Sano et al. |
| 6,982,051 B2 | 1/2006 | St. Onge et al. |
| 6,998,560 B2 | 2/2006 | Ananthanarayanan et al. |
| 7,119,305 B2 | 10/2006 | Sano et al. |
| 7,122,094 B2 | 10/2006 | Baradon et al. |
| 7,223,262 B2 | 5/2007 | Brehm et al. |
| 7,371,305 B2 | 5/2008 | Sano et al. |
| 7,398,813 B2 | 7/2008 | Ivansons et al. |
| 7,484,529 B2 | 2/2009 | Yokota et al. |
| 7,657,996 B2 | 2/2010 | Sano et al. |
| 7,722,733 B2 | 5/2010 | Tomasetti et al. |
| 7,779,880 B2 | 8/2010 | Sano et al. |
| 7,828,788 B2 | 11/2010 | Brehm et al. |
| 7,938,454 B2 | 5/2011 | Buchanan et al. |
| 7,964,048 B2 | 6/2011 | Hlavinka et al. |
| 8,146,642 B2 | 4/2012 | Landherr et al. |
| 8,162,021 B2 | 4/2012 | Tomasetti et al. |
| 8,448,992 B2 | 5/2013 | Min et al. |
| 2002/0174956 A1 | 11/2002 | Sano et al. |
| 2003/0089446 A1 | 5/2003 | Baradon et al. |
| 2006/0005371 A1 | 1/2006 | Sano et al. |
| 2006/0054275 A1 | 3/2006 | Sano et al. |
| 2006/0054613 A1 | 3/2006 | Sano et al. |
| 2006/0144525 A1 | 7/2006 | Sano et al. |
| 2007/0142960 A1 | 6/2007 | Bollinger et al. |
| 2007/0225673 A1 | 9/2007 | Brehm et al. |
| 2008/0009833 A1 | 1/2008 | Corbin et al. |
| 2009/0302033 A1 | 12/2009 | Barr |
| 2010/0133807 A1 | 6/2010 | Bilstad et al. |
| 2010/0137826 A1 | 6/2010 | Watts et al. |
| 2013/0153048 A1* | 6/2013 | Schwalm ............ A61M 39/146 137/15.01 |
| 2014/0034230 A1 | 2/2014 | Wegener et al. |
| 2014/0077488 A1 | 3/2014 | Wegener et al. |
| 2015/0367569 A1 | 12/2015 | Kusters |

FOREIGN PATENT DOCUMENTS

| | | |
|---|---|---|
| EP | 0507321 B1 | 10/1992 |
| EP | 0507321 B1 | 6/1995 |
| EP | 0723851 A2 | 7/1996 |
| EP | 0471953 B1 | 9/1999 |
| EP | 0847847 B1 | 10/1999 |
| EP | 1048316 B1 | 1/2003 |
| EP | 0731540 B1 | 10/2004 |
| EP | 1048315 B1 | 6/2005 |
| EP | 1579983 B1 | 4/2009 |
| EP | 1640142 B1 | 4/2011 |
| EP | 1740366 B1 | 11/2011 |
| EP | 2419257 B1 | 3/2013 |
| EP | 2046560 B1 | 5/2014 |
| EP | 1555111 B1 | 1/2015 |
| EP | 2957402 A1 | 12/2015 |
| JP | S61290035 | 12/1986 |
| JP | H09150458 | 6/1997 |
| WO | WO 8202528 A1 | 8/1982 |
| WO | WO 2012/022635 A2 | 2/2012 |
| WO | WO 2013/048336 A1 | 4/2013 |
| WO | WO 2014/128972 A1 | 8/2014 |
| WO | WO 2015/060774 A1 | 4/2015 |

OTHER PUBLICATIONS

U.S. Appl. No. 13/911,560, filed Jun. 6, 2013 entitled "Bonding Apparatus and Method".

U.S. Appl. No. 14/110,010, filed Oct. 4, 2013, entitled Fluid Flow Conduits and Apparatus and Methods for Making a Joining Fluid Conduits.

* cited by examiner

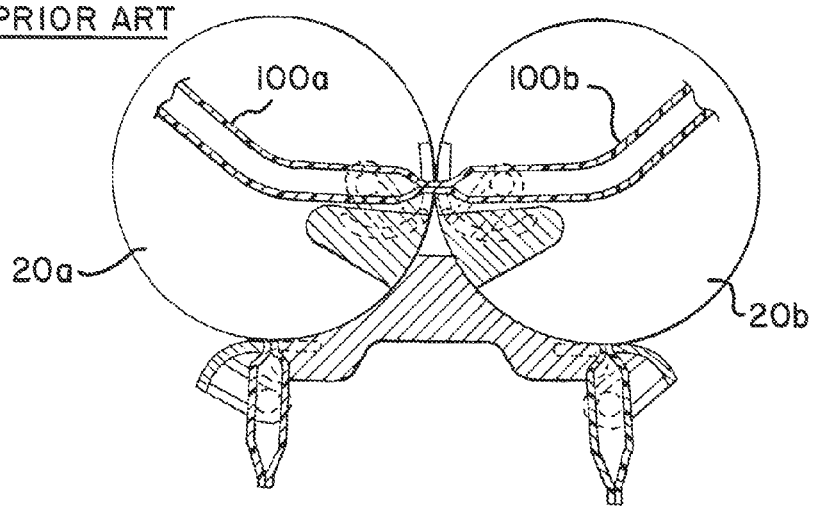
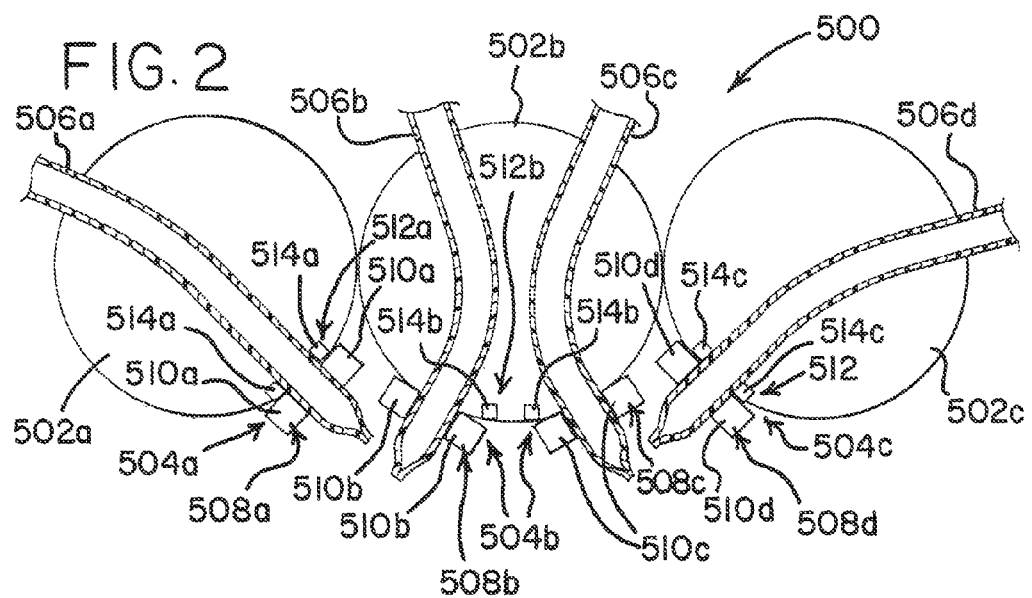

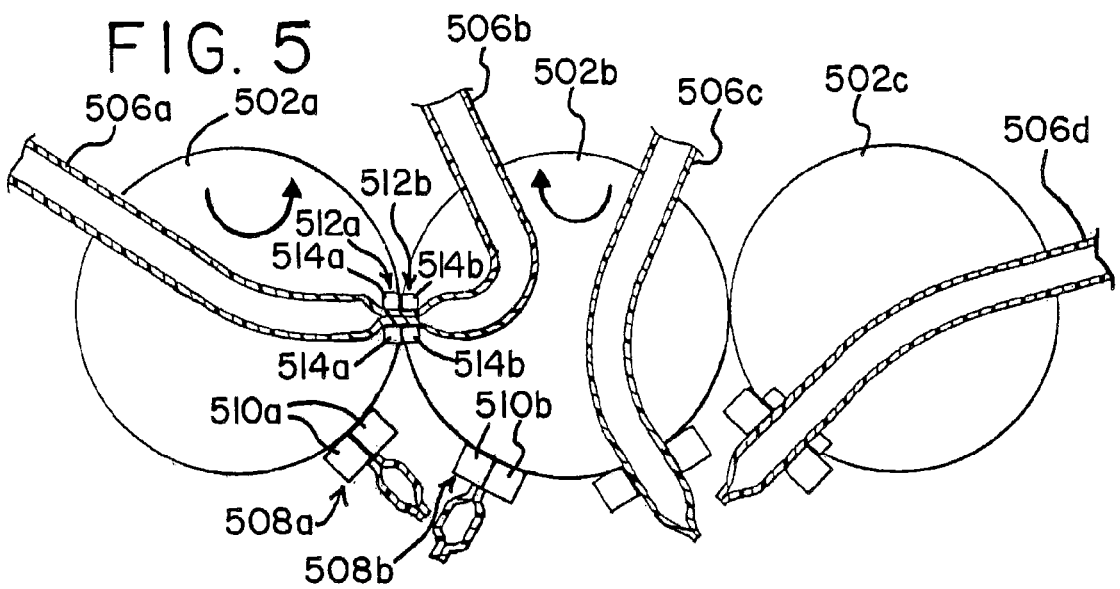
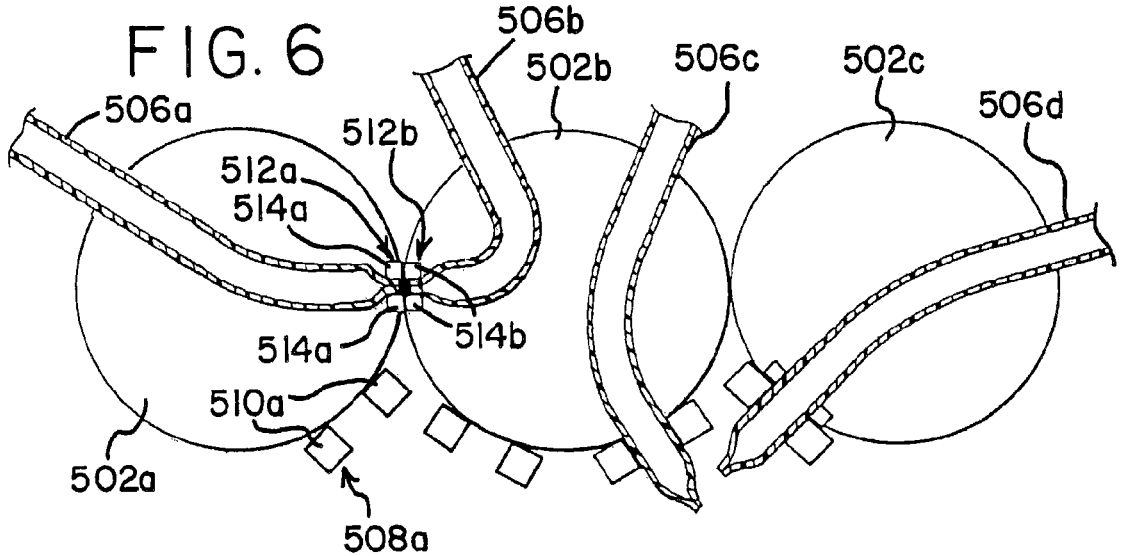

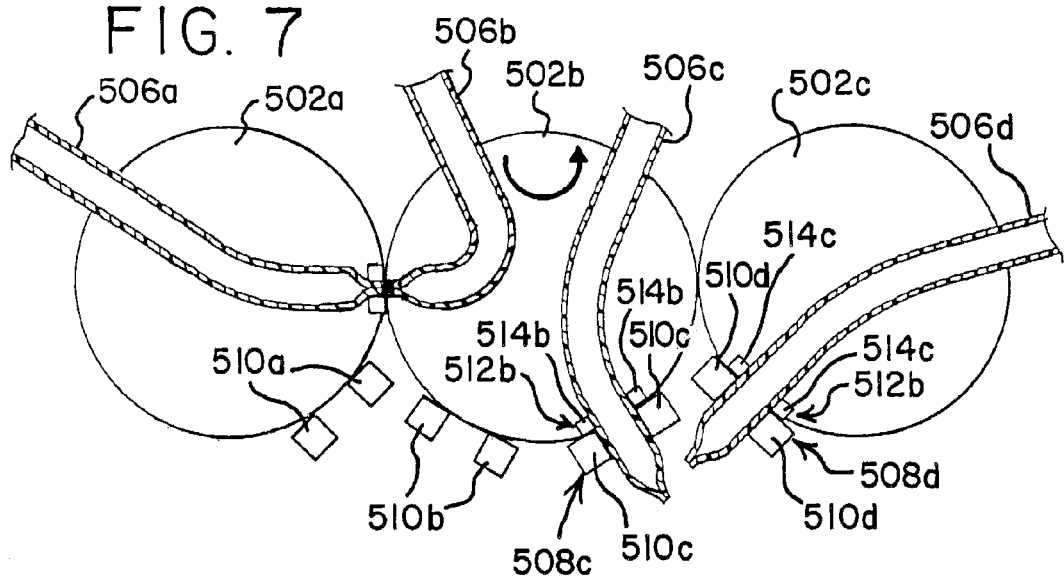
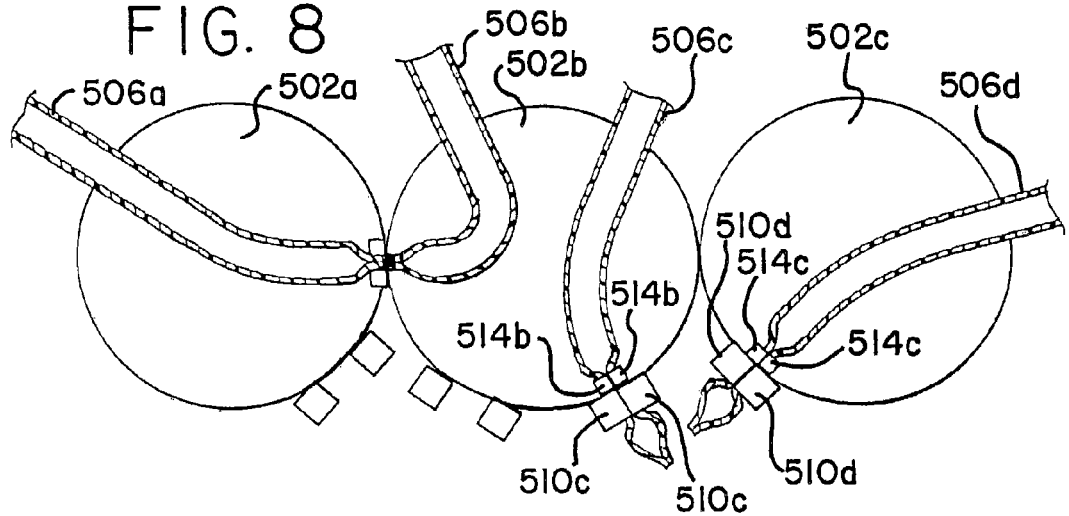

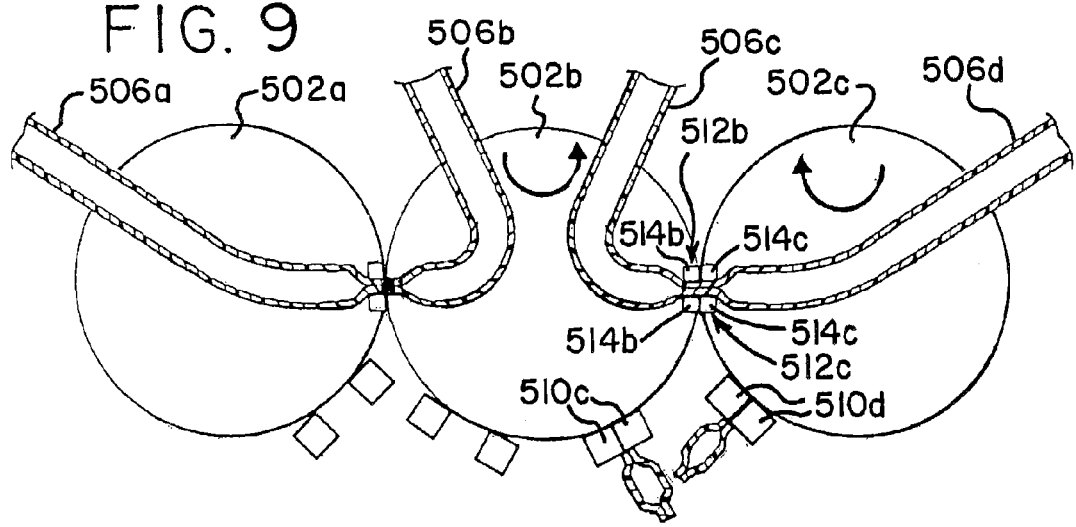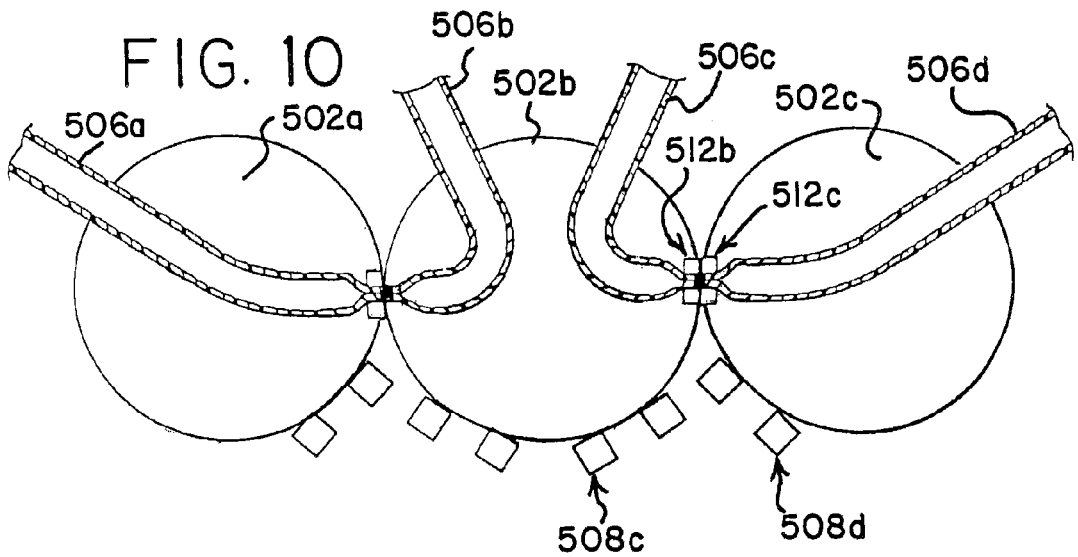

STERILE CONNECTION DEVICE FOR MAKING MULTIPLE CONNECTIONS

The present invention relates generally to apparatus and methods for forming heat or melt-bonded or welded connections, preferably sterile connections, between hollow thermoplastic tubes or tubing such as may be found in medical fluid administration or processing systems, including without limitation, fluid flow systems for collecting, storing or treating blood or blood components.

It is well known in the medical industry in general and particularly in the blood banking field to use so-called sterile connection or docking systems for connecting two separate tubing segments of a fluid flow set or circuit in a manner that prevents the introduction of contaminants and/or preserves the sterility of the tubing, if pre-sterilized, during the connection process.

Such systems have found application both in the large scale assembly or manufacture of fluid flow circuits and in the hands of the ultimate users for on-site assembly of fluid flow circuits having a desired configuration. For example, a user may desire to carry out a particular medical procedure, such as for collecting, processing or treating blood and blood components.

Known sterile connection devices or systems, for example, include electron beam systems, as in U.S. Pat. No. 5,009,645; radiant energy systems that melt facing membranes of fluid flow conduits, as in U.S. Pat. No. 4,157,723; and heated wafer systems that employ wafers for cutting and heat-bonding or splicing tubing segments together while the ends remain at a sufficiently molten or semi-molten elevated temperature, such as in U.S. Pat. Nos. 4,753,697, 5,158,630 and 5,156,701.

More recently, a novel connection system, method and apparatus has been described that connects hollow flexible thermoplastic tubing segments by heat or melt-bonding the ends together while the ends are individually clamped into a closed position, preventing ambient contamination. Such a system is described in detail in U.S. published patent application no. 2013/0153048, which is incorporated by reference herein in its entirety.

The system described in the above application employs a pair of rotating receivers or discs and associated clamping and heating systems for severing heated tubing ends and bringing the tubing into contact while still heated to form an integral bond between them. This apparatus and method works well, but as shown in the published patent application is designed to bond together a single pair of thermoplastic tubes. Without detracting from the benefit or functionality of such apparatus and methods, there is a continuing desire to improve efficiency and reduce costs associated with medical devices and processes.

SUMMARY OF DISCLOSURE

In accordance with a first aspect of the present subject matter, a system is provided for making a plurality of sterile connections between a plurality of pairs of hollow thermoplastic tubes. The system may comprise: a first receiver for receiving a first tube, a first clamping system including a tube heater associated with the first receiver; a second receiver for receiving second and third tubes, a second clamping system including a tube heater associated with the second receiver; and a third receiver for receiving a fourth tube and a third clamping system including a tube heater associated with the third receiver. The first receiver and second receiver may be relatively movable to place clamped and heated ends of first and second tubes into contact to form an integral bond between them; and the second receiver and third receiver may be relatively movable to place clamped and heated ends of third and fourth tubes into contact to form an integral bond between them.

In accordance with a further aspect of the present subject matter, each clamping system may include at least one clamp that is co-movable with the respective receiver with which is associated and at least one clamp that does not move with the respective receiver, whereby movement of the receiver exerts a tensile and/or a shear force on a tube held between such clamps to sever such tube.

In accordance with any of the above aspects of the present subject matter, the first clamping system may include at least one clamp that is co-movable with the first receiver and at least one clamp that does not move with the first receiver; the second clamping system may include at least one clamp that is co-movable with the second receiver and at least two clamps that do not move with the second receiver, and the third clamping system may include at least one clamp that is co-movable with the third receiver and at least one clamp that does not move with the third receiver.

In accordance with any of the above aspects of the present subject matter, the at least one clamp of the second clamping system that is co-movable with the second receiver may also be movable between a position for clamping a second tube and a position for clamping a third tube.

In accordance with any of the above aspects of the present subject matter, at least one of the first and second receivers and at least one of the second and third receivers may be rotatable about an axis of rotation.

In accordance with any of the above aspects of the present subject matter, each of the receivers may be rotatable about its own axis of rotation.

In accordance with any of the above aspects of the present subject matter, each of the receivers may be configured to move a respective tube between a heating position and a bonding position.

In accordance with any of the above aspects of the present subject matter, the first and second receivers may be relatively movable rotatably and laterally relative to their respective axis of rotation and the second and third receivers may be relatively movable rotatably and laterally relative to their respective axis of rotation.

In accordance with any of the above aspects of the present subject matter, the tube heater of each clamping system may comprise a heating element carried by at least one of the clamps of such system for heating a clamped tube.

In accordance with any of the above aspects of the present subject matter, the tube heater of each clamping system may comprise at least one of the clamps of such system defining a high frequency voltage electrode.

In accordance with a further aspect of the present subject matter, a device for sterile connection of thermoplastic tubes may be provided that comprises a first, second and third tubing receivers, each being rotatable about its own axis of rotation, the first receiver including a first clamp system rotatable therewith, the second receiver including a second clamp system rotatable therewith and the third receiver including a third clamp system rotatable therewith. A first relatively stationary clamp system may be associated with the first receiver, a second relatively stationary clamp system may be associated with the second receiver, and a third relatively stationary clamp system may be associated with the third receiver. The first receiver, first rotatable clamping system and first stationary clamping system may be configured to receive and clamp a first tube; the second receiver, second rotatable clamping system and second stationary clamping system may be configured to receive and clamp a second tube and a third tube, and the third receiver, third rotatable clamping system and third stationary clamping system may be configured to receive and clamp a fourth tube. The device may also include a first heater for heating a separation region of a first clamped tubing, a second heater for heating a separation region of a second clamped tubing, a third heater for heating a separation region of a third clamped tubing, and a fourth heater for heating a separation region of a fourth clamped tubing. The respective rotatable and stationary clamping systems may be relatively movable to separate the respective tubing clamped therebetween in the separation region. The first and second receivers may be relatively rotatable about their respective axis of rotation to place heated ends of separated first and second tubes in mechanical contact to form an integral bond with one another and the second and third receivers may be relatively rotatable about the respective axis of rotation to place heated ends of separated third and fourth tubes in mechanical contact to form an integral bond with one another.

In accordance with the above aspect of the present subject matter, at least one of the first stationary and first rotatable clamping systems may include the first heater, at least one of the second stationary and second rotatable clamping systems may include the second and third heaters, at least one of the third stationary and third rotatable clamping systems may include the fourth heater.

In accordance with any of the above aspects of the present subject matter, each heater may comprise a high frequency voltage electrode.

In accordance with any of the above aspects of the present subject matter, the relatively rotatable and stationary clamping systems may also be movable laterally relative to a respective axis of rotation.

In accordance with any of the above aspects of the present subject matter, each of the receivers may comprise a disc having a disc surface on which respective tube or tubes are received and each disc may be rotatable about an axis that is generally perpendicular to the surface of such disc.

In accordance with the above aspect of the present subject matter, the axes of rotation of the discs may be substantially parallel.

In accordance with any of the above two aspects of the present subject matter, the discs of the first receiver and the second receiver may be substantially adjacent and the discs of the second receiver and the third receiver may be substantially adjacent, whereby relative rotation between the discs of the first and second receivers would bring clamped ends of first and second tubes into contact and relative rotation between the discs of the second and third receivers would bring the clamped ends of third and fourth tubes into contact.

In accordance with any of the above three aspects of the present subject matter, the disc of the second receiver may be rotatable in one direction to bring a second tube into contact with a first tube and may be rotatable in the opposite direction to bring a third tube into contact with a fourth tube.

In accordance with any of the above aspects of the present subject matter, the device may include a rotary drive member and a linkage connecting the drive member to the receiver discs, the linkage being operable upon rotation of the drive member to shift the discs laterally between a position wherein the discs of the first and third receivers are spaced apart from the disc of the second receiver and a position wherein the first and third discs are generally adjacent to the disc of the second receiver.

BRIEF DESCRIPTION OF DRAWINGS

The subject matter summarized above and additional subject matter will be more specifically described below, with reference to the embodiments shown for purposes of illustration and not limitation in the attached figures, of which:

FIG. 1C is schematic view of the embodiment of FIG. 1A in yet another operative position.

FIG. 2 is a diagrammatic view of the device or system of the present disclosure illustrating apparatus in a first position for forming heat bonded connections between two different pairs of hollow thermoplastic conduits, such as flexible polyvinyl chloride tubing of a blood processing or collecting system.

FIG. 5 is a diagrammatic view of the device or system of FIG. 2 in a further operative position illustrating movement of first and second clamped tubes to a contacting position.

FIG. 6 is a diagrammatic view of the device or system of FIG. 2 in another operative position illustrating connection of first and second clamped tubes while in a contacting position.

FIG. 7 is a diagrammatic view of the device or system of FIG. 2 in a further operative position illustrating movement of a clamp on a second receiver to engage a third tube.

FIG. 8 is a diagrammatic view of the device or system of FIG. 2 in another operative position illustrating clamping of third and fourth tubes.

FIG. 9 is a diagrammatic view of the device or system of FIG. 2 in yet a further operative position illustrating movement of third and fourth clamped tubes to a contacting position.

FIG. 10 is a diagrammatic view of the device or system of FIG. 2 in another operative position illustrating connection of third and fourth clamped tubes while in a contacting position.

DETAILED DESCRIPTION

Figure 1A:
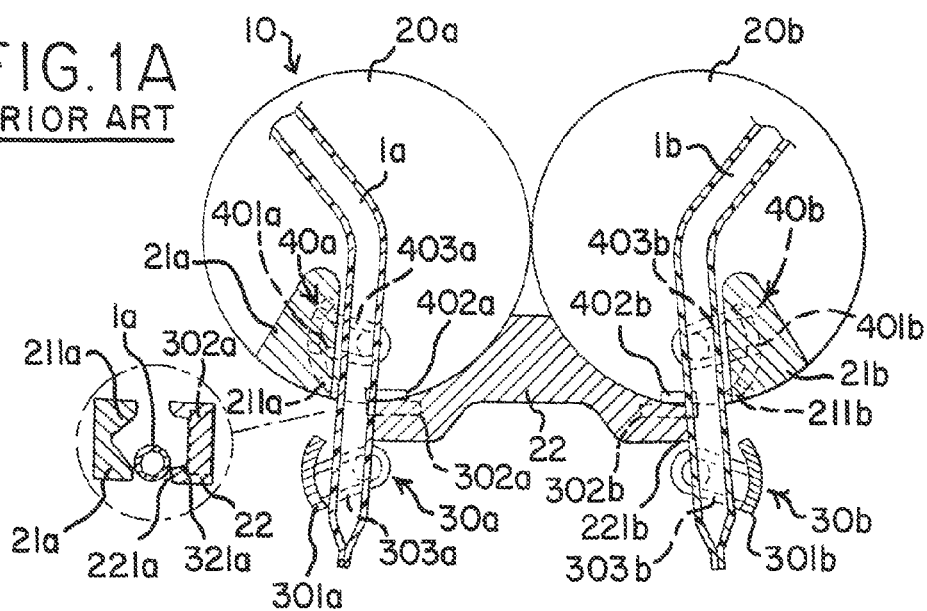
FIG. 1A is schematic view of one embodiment of the device of the published U.S. application no. 2013/0153048 and is included here for purposes of description of the structure and operation of the present subject matter.

Turning now to a more detailed description of the attached drawings, according to FIG. 1A, the device 10 comprises a first receiving device in the form of a first disk 20*a* and a second receiving device in the form of a second disk 20*b*. The disks 20*a*, 20*b* are each mounted rotatably about an axis of rotation that extends perpendicularly to the respective main faces of said disks and through the midpoint thereof.

A first tube 1*a* is received on the first disk 20*a* and a second tube 1*b* is received on the second disk 20*b*. The tubes 1*a*, 1*b* are each guided along a receiving body 21*a*, 21*b* arranged on the respective disk 20a, 20b, wherein the receiving bodies 21a, 21b each have a groove 211a, 211b for guiding the tube (see the detail of the device 10 illustrated in cross section in the bottom left-hand corner next to the primary illustration in FIG. 1A), which extends at least over part of a side of the prism-like receiving body 21a, 21b facing the tube 1a or 1b respectively.

The device 10 further comprises a guide body 22, which is assigned jointly to both disks 20a, 20b, (but is arranged separately relative thereto) and comprises a first groove 221a facing the first tube 1a and a second groove 221b facing the second tube 1b, which are used to guide the respective tube; see the cross-sectional illustration already mentioned above of a detail of the device 10 in FIG. 1A.

In addition, the device 10 comprises two clamping devices 30a, 30b, which are assigned to the first disk 20a and to the second disk 20b respectively. The clamping devices 30a, 30b have a clamping jaw 301a, 301b respectively, which are mounted rotatably about an axis of rotation extending perpendicularly to the main face of the disks 20a, 20b (that is to say also perpendicularly to a plane or longitudinal axis along which the tube 1a, 1b extends at least in the region of the receiving body 21a, 21b). The tubes 1a, 1b are clamped respectively between the clamping jaws 301a, 302a and 301b, 302b by rotation of the clamping jaws 301a, 301b.

The device 10 also comprises two clamping devices 40a, 40b, which are likewise assigned to one of the disks 20a, 20b respectively. The clamping devices 40a, 40b have a respective clamping jaw 401a, 401b arranged on the disk 20a, 20b, but rotatable relative to the respective disks 20a, 20b, and a clamping jaw 402a, 402b arranged fixedly (non-rotatably) on the disks 20a, 20b. By rotating the clamping jaws 401a, 401b in the direction of the clamping jaws 402a, 402b respectively, the tube can be clamped above the clamping device (that is to say on a side of the first clamping device 30a, 30b facing away from the free end of the tubes 1a, 1b). For example, the clamping jaws 401a, 401b are guided within a correspondingly embodied recess in the respective receiving body 21a, 21b.

Once the tubes 1a, 1b have been inserted into the respective groove 211a, 221a or 211b, 221b in the receiving bodies 21a, 21b and the guide body 22, the disks 20a, 20b are rotated slightly toward the guide body 22, that is to say the first disk 20a rotates in an anti-clockwise direction and the second disk 20b rotates in a clockwise direction, such that the receiving bodies 40a, 40b are moved toward the guide body 22, whereby the tube 1a, 1b is clamped slightly between the receiving bodies 40a, 40b and the groove 221a, 221b, assigned to the respective tube 1a, 1b, in the guide body 22.

The device 10 further comprises heating means for heating a separating region of the tubes 1a, 1b, in which a first tube portion in the form of the main tube portion 100a, 100b and a second tube portion in the form of an end tube portion 101a, 101b adjoin one another respectively. The heating means are designed in the form of high-frequency voltage generation means (in particular comprising a high-frequency voltage source, which are electrically connected to the second, metal clamping jaws 302a, 302b ("hot electrodes") of the first clamping devices 30a, 30b and which introduce a high-frequency voltage into the clamping jaws 302a, 302b after activation.

The movable clamping jaws 301a, 301b are at earth potential in particular. The HF clamping jaws 302a, 302b are arranged in a recess in the guide body 22 adjoining the grooves 221a, 221b, the guide body possibly being formed from an electrically insulating material, for example at least in part. The HF clamping jaws 302a, 302b are additionally positioned such that they each adjoin the groove 221a, 221b via a substantially flat clamping side 3021a, 3021b, with which they bear against the tube in the clamped position of the clamping devices 30a, 30b and introduce the high-frequency voltage into the tube, that is to say the clamping sides 3021a, 3021b form a base of the respective groove.

Figure 1B:
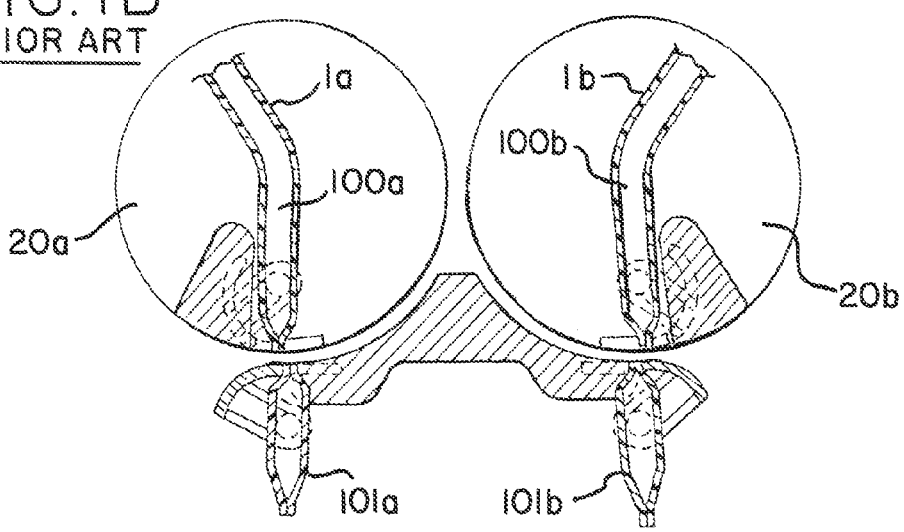
FIG. 1B is schematic view of the embodiment of FIG. 1A in a different operative position.

The high-frequency voltage generation means generate via the clamping jaws 301a, 302a, 301b, 302b an electrical high-frequency field in the separating region of the tubes 1a, 1b (that is to say in a region in the vicinity of the clamping jaws 301a, 301), which heats each of the tubes in this separating region. Once the separating region has been heated or during the heating process, a movement of the disks 20a, 20b away from the first clamping devices 30a, 30b is initiated (see FIG. 1B). The device 10 has movement generation means in order to generate this movement.

Due to the movement of the disks 20a, 20b away from the first clamping devices 30a, 30b, a tensile and shear force is exerted onto the tubes 1a, 1b, such that they are drawn away from one another in the separating region and are ultimately torn apart from one another, that is to say the main tube portions 100a, 100b are separated or severed from the end tube portions 101a, 101b. It is noted that the movement of the disks 20a, 20b illustrated in FIG. 2c is not absolutely necessary to separate the tubes. Rather, it is also conceivable that a separating force is generated by displacing the disks 20a, 20b merely in rotation about their axis of rotation extending through their midpoint, without moving the disks 20a, 20b away from the guide body 22.

A smooth tear-off edge is produced in particular between the tube portions 100a, 101a and 100b, 101b above the clamping jaws 301a, 302a, 301b, 302b (that is to say the "hot" HF electrodes), which is attributed in particular to the fact that an improved transport of heat from the tube 1a, 1b is produced via the clamping jaws 301a, 301b formed from metal compared to the transport of heat in the region above the clamping jaws 301a, 301b (that is to say in the region between the clamping jaws 301a, 301b and the clamping jaws 401a, 401b of the clamping device 40a, 40b), whereby a temperature gradient occurs in the tube on the upper side (that is to say a side facing toward the second clamping device 40a, 40b) of the first clamping jaws 401a, 401b, wherein the tubes are preferably torn apart from one another in the region of this temperature gradient under the influence of the tensile or shear force. In particular, the temperature gradient exists at the surface of the tubes, wherein it is possible for the surface of the tubes to have a greater temperature between the clamping devices 30a, 30b and 40a, 40b than the surface of the tubes in the region of the first clamping devices 30a, 30b (that is to say between the clamping jaws 301a, 302a and 301b, 302b). In particular, the clamping jaws used as high-frequency electrodes have a flat side, via which they bear against the tube in the clamped position so as to generate a most uniform field possible in the tube and also to implement the best possible dissipation of heat away from the tube.

Once the tubes 1a, 1b have been separated into the main tube portions 100a, 100b and the end tube portions 101a, 101b, the disks 20a, 20b are rotated in such a way that the ends of the main tube portions 100a, 100b produced by the separation of the tubes 1a, 1b and held by the clamping devices 40a, 40b are moved toward one another; see FIG. 1C. To this end, the first disk 20a is rotated in an anti-clockwise direction about the axis of rotation oriented perpendicularly to the main faces of the disk and therefore also perpendicularly to a plane along which a part (that runs in the region of the receiving body 40a) of the main tube portion 100a extends. An analogous rotational movement is performed by the second disk 20b, but in a clockwise direction.

The disks 20a, 20b are each rotated about approximately 90 degree, such that the two ends of the main tube portions 100a, 100b lie opposite one another along a common longitudinal axis after the rotation of the disks 20a, 20b. The two disks 20a, 20b are then moved toward one another such that the end faces of the ends of the main tube portions 100a, 100b lying opposite one another along the common longitudinal axis contact one another (FIG. 1C). In particular, the disks 20a, 20b are rotated about their respective axis of rotation and the disks are moved toward one another so quickly that the ends of the main tube portions 100a, 100b, as a result of the heating according to FIG. 2b, still have such a temperature even once the heating means have been switched off that they form an integral bond with one another, that is to say are welded to one another, when they come into mechanical contact with one another in accordance with FIG. 1C, without the need for renewed heating.

After a cooling phase (for example at least 4 seconds), the clamping jaws 401a, 401b of the clamping device 40a, 40b can also be released and the tube produced by connection of the main tube portions 100a, 100b can be removed from the device 10. The invention is of course not limited to a specific cooling time; shorter or longer cooling times may also be necessary, for example according to the nature of the tube. In particular, the tube must have sufficient strength after the cooling time so that it can be removed reliably from the device and used.

Understanding the operation and structure of the two disc system described above, attention is now directed to the present subject matter shown in FIGS. 2-16. The device shown there may be part of a free-standing device for heat-bonding tubings, or may be part of a larger fluid processing system, for example a device for processing blood or blood components. While shown diagrammatically, the present subject matter is intended to employ many of the same structures, for example certain receiver discs, tube clamping arrangements and tube heating devices as described above, so details of those will not be repeated.

Turning now to FIG. 2, the illustrated sterile connection system/apparatus 500 provides sterile connections between a plurality of pairs of hollow thermoplastic conduits (e.g., tubes) without requiring two full sets of all the apparatus described above, thereby providing potential cost and efficiency benefits. As seen in FIG. 2, the device 500 includes a first tube receiver in the form of a disc 502a, a second tube receiver in the form of a disc 502b and a third tube receiver in the form of disc 502c. In the illustrated embodiment, each disc can pivot or rotate about its own central axis of rotation and can move laterally relative to its axis of rotation and to the other discs.

A first clamping system, generally at 504a, is associated with the first disc 502a for engaging a first thermoplastic tube 506a, a second clamping system, generally at 504b, is associated with the second disc 502b for engaging second and third thermoplastic tubes 506b and 506c, and a third clamping system, generally at 504c, is associated with the third disc 502c for engaging a fourth thermoplastic tube 506d. Except as otherwise described, the clamps of the present subject matter may be the same or similar to the clamping structures described in detail above, which detail will not be unnecessarily repeated.

First clamping system 504a includes a clamping device 508a, which does not move with rotation or lateral movement of the first disc 502a and may be relatively stationary. Second clamping system 504b includes two clamping devices, 508b and 508c, which do not move with rotation or lateral movement of the second disc 502b and may be relatively stationary. Third clamping system 504c includes a clamping device 508d, which does not move with rotation or lateral movement of the third disc 502c and may be relatively stationary. Each clamping device 508a-d may have a pair of opposed clamping jaws, 510a-d respectively, for clamping one of the tubes 506a-d therebetween. As seen in FIG. 2, each pair of clamping jaws 510a-d is located generally adjacent to a peripheral edge the particular disc 502 with which it is associated.

Each clamping system 504a-c also includes at least one clamping device 512a-c that is co-movable with and may be situated on or in the respective disc 502a-c with which the clamping system is associated. More specifically, clamping device 512a of the first clamping system 504a, has a pair of opposed clamping jaws 514a located on the first disc 502a for clamping the first tube 506a therebetween.

Figure 16A:
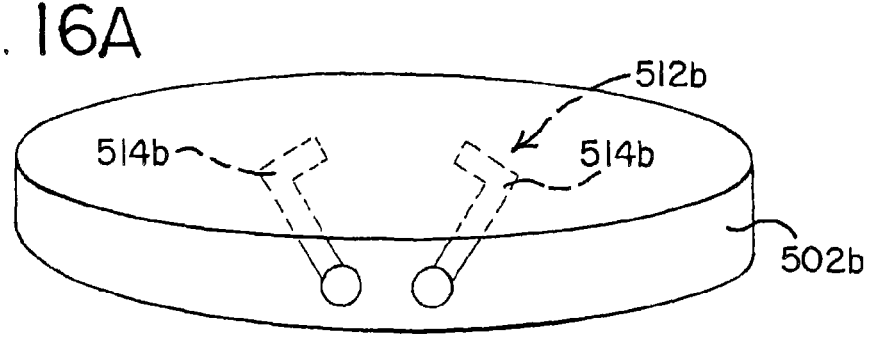
FIGS. 16A and 16B illustrate one form of a clamp on a receiver disc that may be opened or closed to clamp tubing.
Figure 16B:
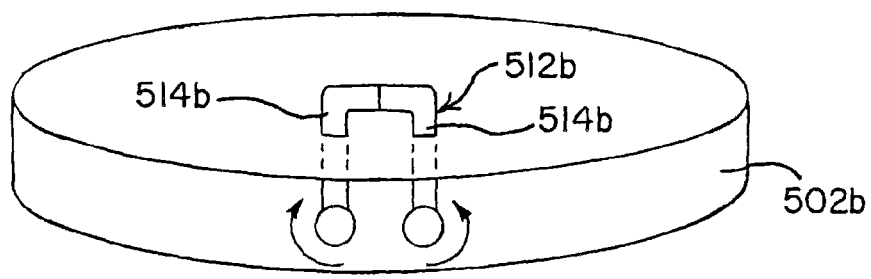

Clamping device 512b of the second clamping system 504b, has a pair of opposed clamping jaws 514b located on the second disc 502b for clamping either of the second and third tubes 506b-c therebetween. The movement of the clamping device 512b to alternately clamp the two tubes 506b and 506c, and how that may occur, may be better understood with reference to FIGS. 16A-B. It should be understood that as presently contemplated, second and third tubes 506b and 506c simply overlie or rest on the upper surface of the second disc 502b and the disc may rotate beneath them. As seen in FIGS. 16A-B, clamping device 512b is mounted in disc 502b with each jaw 514b pivotally mounted to move between an open position (FIG. 16A) in which the jaws are generally recessed flush with or below the upper surface of disc 502b and a closed or clamping position (FIG. 16B) in which they extend above the surface of the disc to clamp the appropriate tube. With rotation of the second disc 502b, the clamp can, after opening to release one of the tubes following sterile connection of that tube, be moved to a position below the other tube for clamping that tube to carry out the sterile connection process. The recessed location of the open jaws allows the disc to rotate beneath the tubes without interfering with or snagging the tubes. FIGS. 16A-B simply illustrate one form of clamping device 512b that may be suitable, and is not intended to limit the present disclosure to the particular structure shown. Optionally, the illustrated configuration of clamping device 512b could also be used for the other clamping devices 512a and 512c on the first and third discs if desired.

Finally, clamping device 512c of the third clamping system 504c, has a pair of opposed clamping jaws 514c located on the third disc 502c for clamping the fourth tube 506d therebetween. As may be seen in FIG. 2, the clamping devices 512a-c are preferably located generally adjacent to or in proximity to the peripheral edges of the respective discs. This permits the movable clamping devices 512 to be positioned via rotation of the respective discs adjacent to and in general alignment with the respective relatively stationary clamping devices 508. This adjacent positioning also serves to accommodate insertion of one of the tubes 506 and servicing of the tubes upon relative movement between the movable and stationary clamping devices, as will become more apparent in the description that follows. More specifically and to avoid any confusion, movable clamping device 512a can be brought into general alignment with relatively stationary clamping device 508a for receiving first tube 506a; movable clamping device 512b and be brought into general alignment with relatively stationary clamping devices 508b and 508c for receiving second or third tubes 506b and 506c; and movable clamping device 512c and be brought into general alignment with relatively stationary clamping device 508d for receiving fourth tube 506d.

As also described in detail earlier, each clamping system includes a heating structure to heat the respective thermoplastic tube that is clamped therein. Various heating arrangements and/or methodologies may be used, and as described earlier, one of the relatively stationary or movable clamps may include a heating element that can be electrically energized, and more specifically the jaws of one of the clamps may be opposed electrodes (hot and ground) of a high frequency voltage system.

The tubes may be associated with any part of a fluid flow system or system component, not shown. For example, tubes 506b and 506c may be tubing segments of a larger pre-sterilized fluid flow circuit or system. Tube 506a may be a tubing flow segment extending from a container of additive or other fluid used in the process, such as red blood cell additive solution, and tube 506d may be a flow tubing segment attached to a container of blood previously collected from a donor. The arrangement of the present subject matter allows the tubing segments to be positioned on the apparatus by the user and a connection sequence started that will automatically connect two pairs of tubing segments without further user intervention or manipulation.

This sequence of steps is shown in FIGS. 2-10. In FIG. 2, an initial tube loading position, the relatively movable clamping device 512b of the second clamping system 504b, is shown in an optional initial or neutral position, located between the second and third tubes 506b and 506c. Tube 506a is positioned between the aligned clamping jaws of clamping devices 508a and 512a, tube 506b is positioned between the clamping jaws of stationary clamping device 508, tube 506c is positioned/located between the clamping jaws of stationary clamping device 508, and tube 506d is positioned/located between aligned jaws of clamping devices 508d and 512c.

Figure 3:
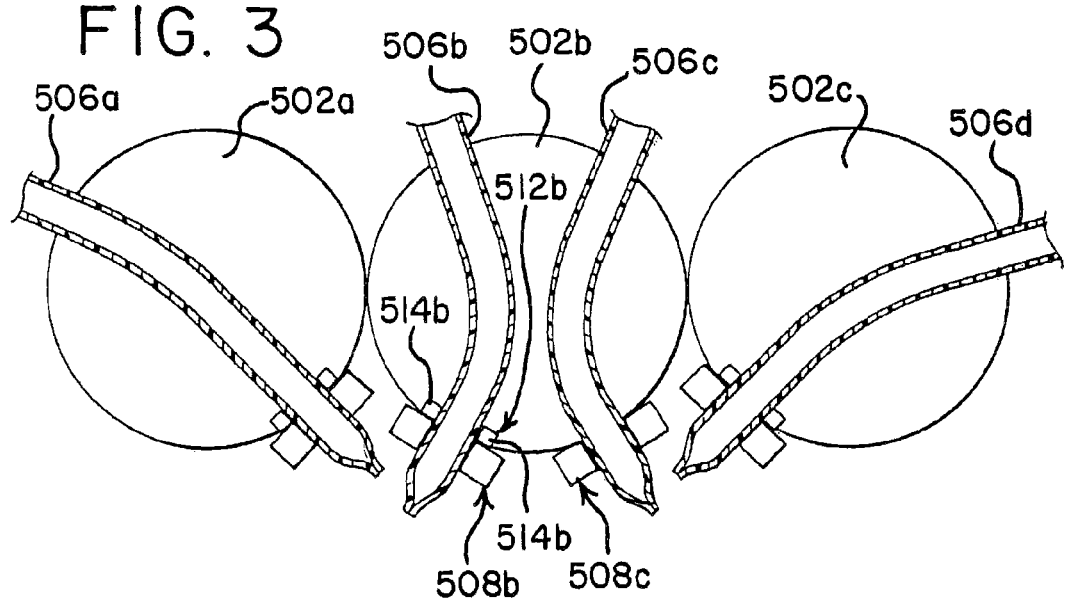
FIG. 3 is a diagrammatic view of the device or system of FIG. 2 in another operative position illustrating tubes arranged within associated clamping devices.

In FIG. 3, the clamping device 512b has been rotated clockwise, such as by rotating the second disc 502b, to a position in alignment with relatively stationary clamping device 508b to engage the second tube 506b. This could also be the initial starting or tube loading position if desired.

Figure 4:
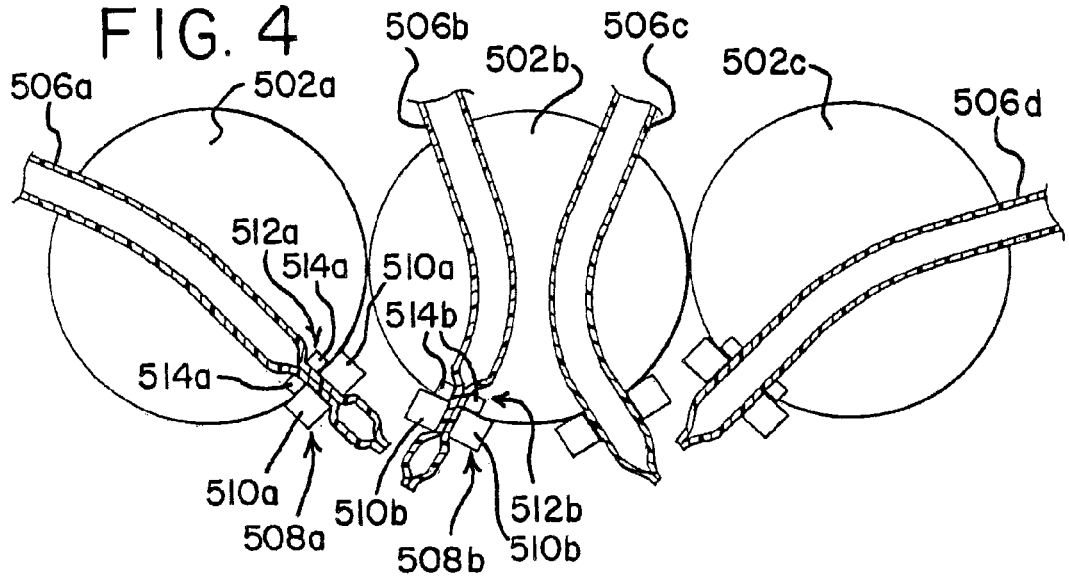
FIG. 4 is a diagrammatic view of the device or system of FIG. 2 in a further operative position illustrating clamping of first and second tubes.

Referring to FIG. 4, the jaws of the relatively stationary and movable clamps 508a, 512a, 508b and 512c are then closed to clamp the tubes 506a and 506b in a closed and sealed clamped position. A heater associated with at least one of the relatively movable or stationary aligned clamps may then be activated to raise the temperature of the respective thermoplastic tube sufficiently, such as for example to a molten or semi-molten state, to allow it to be separated or severed by relative movement between the movable clamping devices 512a and 512b and the relatively stationary clamping devices 508a and 508b. As described above, the heating may be provided by a separate heater or heating device, or the jaws of one of the clamping devices may include or act as a heating element, such as a high frequency voltage electrode, to heat the tube material.

The movement as between the relative stationary clamping devices 508a and 508b and the movable clamping devices 512a and 512b can occur by rotation of the movable clamps relative to the stationary clamps, lateral separation of the movable clamps from the stationary clamps or both rotation and lateral shifting. FIG. 5 illustrates rotation of the movable clamping devices 512a and 512b and associated disc 502a and 502b relative to the stationary clamping devices 508a and 508b to sever the tubes. Apparatus, such as shown in FIGS. 11-15, which will be described later, may also be provided to cause lateral shifting of the clamping devices.

Returning to FIG. 5, that figure illustrates counterclockwise rotation of the relatively movable clamping device 512a and clockwise rotation of clamping device 512b (either independently or with rotation of the associated disc 502a and 502b) to a position where the severed and clamped ends of the tubes are brought into alignment and contact. As described earlier, this rotation occurs promptly after heating so the severed ends remain sufficiently hot, even without supplemental heating, to bond or weld to one another.

The tubes are held in the contacting position for a short period of time sufficient for the tubes to cool and the connection to solidify sufficiently to be released from the clamping jaws (see FIG. 6) Also, the relative stationary clamps 508a and 508b may be opened at any time to release the severed distal ends of the tubes.

Next, as best seen in FIG. 7, the relatively movable clamping device 512b is rotated, with the second disc 502b or independently, to a position in alignment with stationary clamping device 508c to engage the third tube 506c. As previously described with reference to FIG. 16, the clamp 512b may be mounted on the disc 502b for movement between an open position in which it is recessed flush or below the surface of the disc and a closed or clamping position wherein it projects above the surface of the disc so as to be able to move freely between and to engage and clamp one of the tubes 506b or 506c.

As shown in FIG. 7, the relative movable and stationary clamping devices 512b, 508c, 512c and 508d are now positioned ready to process and connect tubes 506c and 506d without the need for user intervention.

Turning to FIG. 8, the jaws 514b and 514c of the relatively movable clamping devices 512b and 512c and the jaws 510c and 510d of the relatively stationary clamping devices 508c and 508d are closed, clamping and sealing the third and fourth tubes 506c and 506d.

The heater of each clamping system is activated and after the respective tubes 506c and 506d are heated, movable clamping device 512b is then rotated (with disc 502b or independently) counterclockwise and movable clamping device 512c is then rotated (with disc 502c or independently) clockwise. This movement alone or together with a lateral shifting apart of the clamps separates or severs the tubes 506c and 506d as previously described, and the clamped and heated ends of the tubes are rotated until in a facing and contacting relationship as shown in FIG. 9. There, they are held until the tube ends are sufficiently cool to solidify the connection. In the meantime the stationary clamping devices 508c and 508d may be opened and the severed ends of the tubes released for disposal. The joined tubing pairs are released from the relatively movable clamps, and after user confidence that the connection is open, the connected tubes are ready for use.

Thus, the present apparatus, whether used as a standalone sterile connection device or as part of a large piece of processing equipment, provides the ability to form multiple heat bonded connections between a plurality of tube pairs, with only limited user involvement needed.

Figure 11:
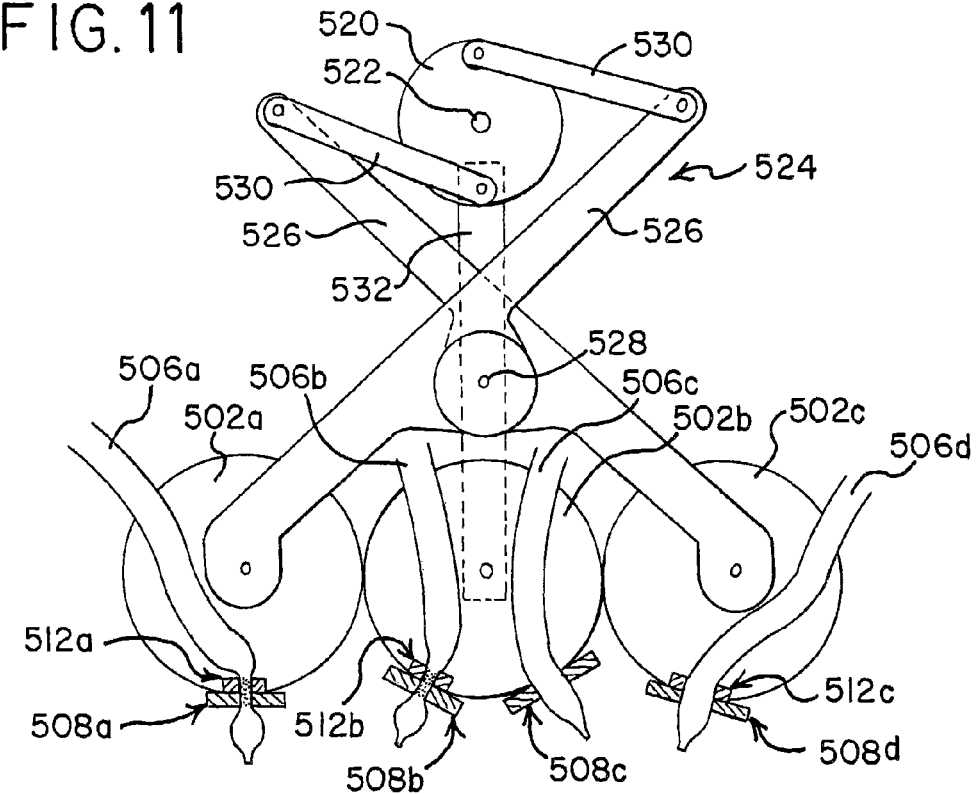
FIGS. 11-15 are diagrammatic view of apparatus of the present subject matter for moving tubing receivers between spaced apart and adjacent positions and illustrating the receivers in different operative positions.

Turning now to FIGS. 11-15, FIG. 11 shows one example of apparatus for moving the discs between adjacent positions and laterally spaced apart positions. As seen in FIG. 11, and in the other figures, the discs 502a-c are generally positioned in an inline or side by side relationship, with parallel axes of rotation. The illustrated apparatus includes a rotary drive member 520 mounted for rotation or pivoting about a central axis 522, which drive member may be rotated by an electrical motor, for example a stepper motor, a solenoid, or other electrical, hydraulic or pneumatic drive. The drive member 520 is connected to the discs 502a and 502c by a linkage that includes a scissors linkage generally at 524 having a pair of legs 526 pivotally mounted for rotation about axis 528. Each leg has one end attached to the drive member 520 by an intermediate linkage 530. The opposite end of each leg is attached generally axially to one of the discs 502a and 502c. The intermediate linkages 530 are eccentrically and pivotally attached to the drive member 520 so that rotation or pivoting of the drive member spreads the ends of the scissor legs, moving first and third discs 502a and 502c and the associated movable clamping devices 512a and 512c laterally away from the relatively stationary clamping devices 508a and 508d. The motion also optionally moves the first and third discs to a spaced apart position relative to the center second disc 502b.

Figure 15:
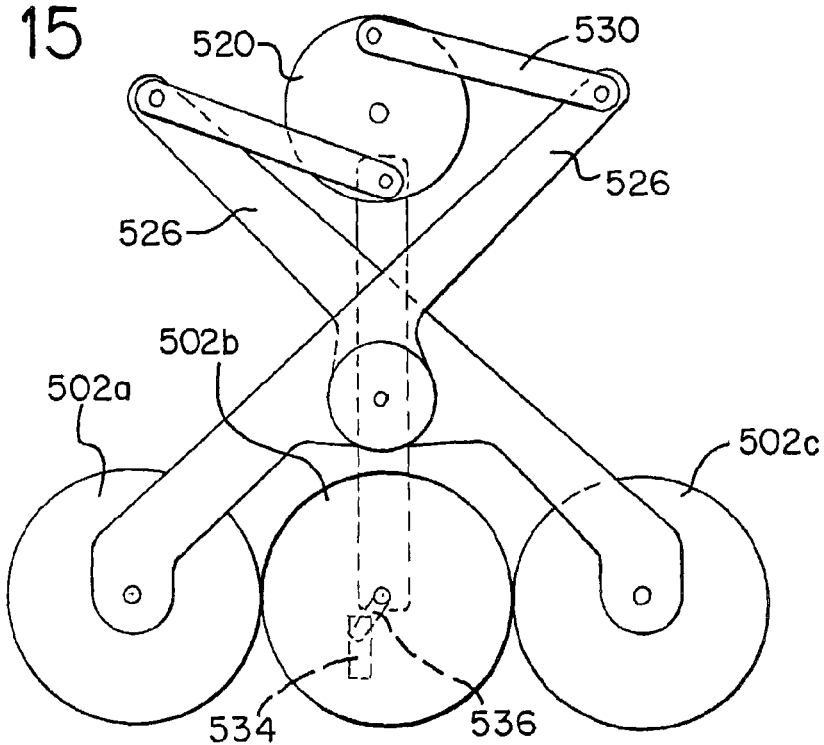

Another linkage 532 connects the drive member 520 to the second disc 502b. The linkage 532 has one end that is mounted eccentrically and pivotally to the drive member, and another end that is axially attached to second disc 502b. Rotation of the drive member shifts the disc 502b and the associated movable clamping device 512b laterally from the relatively stationary clamping devices 508b and 508c. Optionally, the lateral movement of the second disc 502b can be constrained so that the linkage 532 can only move the disc in a limited direction, such as vertical as seen from the perspective of FIG. 11. Referring to FIG. 15, this may be achieved or accommodated by any suitable connection arrangement between the linkage 532 and the second disc 502b. As illustrated in FIG. 15, a slot or track 534 may be provided below the disc and the disc may have a follower pin 536 that projects into the track to allow the linkage to move the second disc only in the direction of the slot.

Returning to FIGS. 11-14, FIG. 11 is comparable to FIG. 4, showing the linkage 522 positioning the discs 502a-c adjacent to one another and with tubes 506a and 506b clamped, respectively, by the clamping devices 508a and 512a (for tube 506a) and the clamping devices 508b and 512b (for tube 506b).

Figure 12:
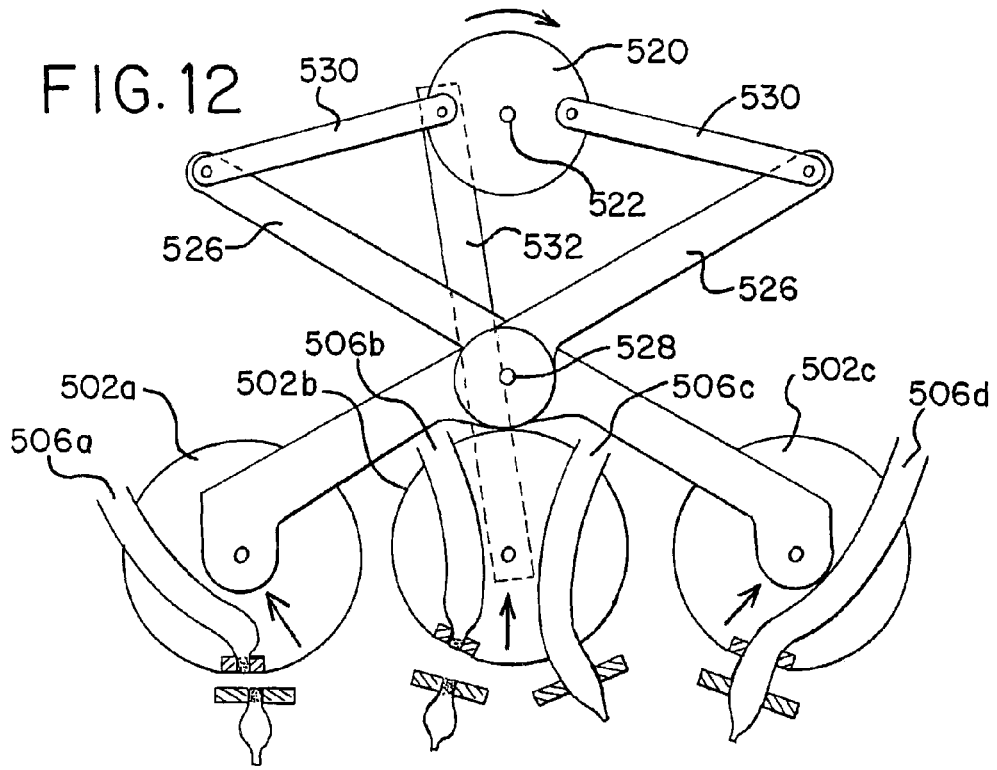

FIG. 12 illustrates the linkage 522, after the clamped tubes 506a-b have been heated, moving the discs 502a-c and respective movable clamps 512a-b away from the stationary clamping devices 508a-b to separate or sever the clamped tubes.

Figure 13:
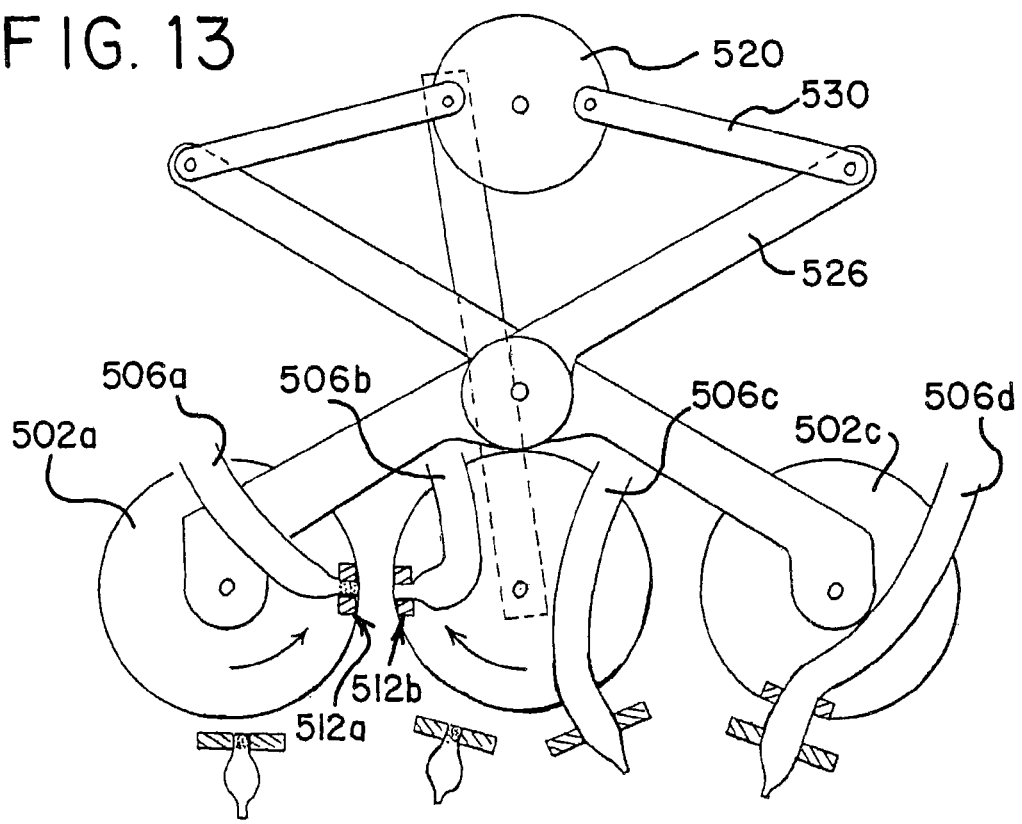
Figure 14:
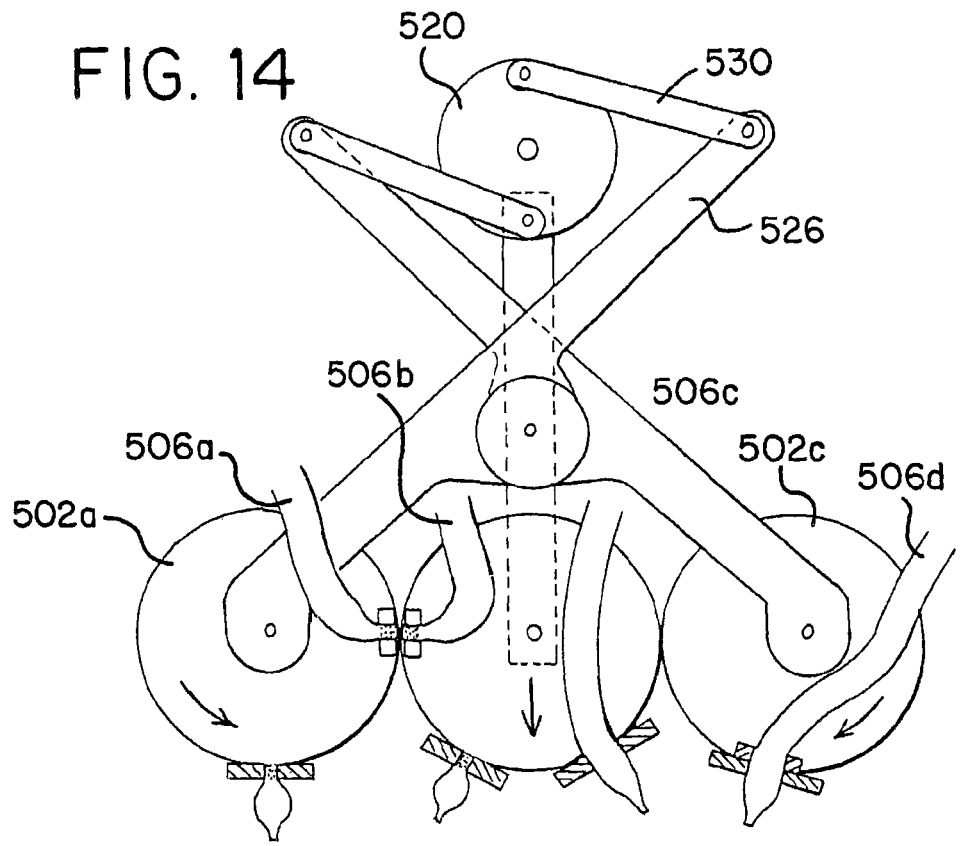

In FIG. 13 the discs 502a and 502b have been rotated while in the displaced position of FIG. 12, bringing the heated and clamped ends of tubes 506a and 506b into a facing relation. Then, as seen in FIG. 14, the drive member 520 is rotated in a reverse direction, returning the linkage 524 to the earlier position, where the discs are adjacent and bringing the clamped ends of the tubes 506a-b into direct contact to form a bond or weld therebetween.

After sufficient cooling time, a matter of a few seconds, the movable clamping devices 512a-b are opened and the joined tubes 506a-b released. The second disc 502b and clamping device 512b is then rotated to place the clamping device 512b into engagement with tube 506c and the process is then repeated with respect to discs 502b-c and clamping devices 512b, 508c, 512c and 508d to form a heat-bonded connection between tube 506c and tube 506d, as described above.

While the present subject matter has been described with reference to specific examples or embodiments, that is for the purpose of description and not limitation. The scope of the present subject is as found in the appended claims.

The invention claimed is:

1. A system for making a plurality of sterile connections between a plurality of pairs of thermoplastic tubes, the system comprising:
   a first receiver for receiving a first tube, a first clamping system including a first tube heater associated with the first receiver;
   a second receiver for receiving second and third tubes, a second clamping system including a second tube heater associated with the second receiver;
   a third receiver for receiving a fourth tube, a third clamping system including a third tube heater associated with the third receiver;
   the first, second and third tube heaters being separate from one another;
   the first receiver and second receiver being relatively movable to place clamped and heated ends of first and second tubes into contact to form an integral bond between them; and
   the second receiver and third receiver being relatively movable to place clamped and heated ends of third and fourth tubes into contact to form an integral bond between them.

2. The system of claim 1 in which each clamping system includes at least one clamp that is co-movable with the respective receiver with which is associated and at least one clamp that does not move with the respective receiver, whereby movement of the receiver exerts a tensile and/or a shear force on a tube clamped between such clamps of such respective system to sever such tube.

3. The system of claim 2 in which at least one of the first and second receivers and at least one of the second and third receivers is rotatable about an axis of rotation.

4. The system of claim 2 in which each of the receivers is rotatable about its own axis of rotation.

5. The system of claim 2 in which the tube heater of each clamping system comprises a heating element carried by at least one of the clamps of such system for heating a clamped tube.

6. The system of claim 2 in which the tube heater of each clamping system comprises at least one of the clamps of such system defining a high frequency voltage electrode.

7. The system of claim 1 in which the first clamping system includes at least one clamp that is co-movable with the first receiver and at least one clamp that does not move with the first receiver, the second clamping system includes at least one clamp that is co-movable with the second receiver and at least two clamps that do not move with the second receiver, and the third clamping system includes at least one clamp that is co-movable with the third receiver and at least one clamp that does not move with the third receiver.

8. The system of claim 7 in which the at least one clamp of the second clamping system that is co-movable with the second receiver is also movable between a position for clamping a second tube and a position for clamping a third tube.

9. The system of claim 1 in which each of the receivers is configured to move a respective tube between a heating position and a bonding position.

10. The system of claim 1 in which each of the first, second and third receivers has a respective axis of rotation and each of the first and second receivers is relatively movable rotatably and laterally relative to their respective axis of rotation and the second and third receivers are relatively movable rotatably and laterally relative to their respective axis of rotation.

11. A device for sterile connection of tubes comprising:
first, second and third tubing receivers, each being rotatable about its own axis of rotation, the first receiver including a first clamp system rotatable therewith, the second receiver including a second clamp system rotatable therewith and the third receiver including a third clamp system rotatable therewith;
a first relatively stationary clamp system associated with the first receiver, a second relatively stationary clamp system associated with the second receiver, and a third relatively stationary clamp system associated with the third receiver;
the first receiver, first rotatable clamping system and first stationary clamping system being configured to receive and clamp a first tube; the second receiver, second rotatable clamping system and second stationary clamping system being configured to receive and clamp a second tube and a third tube, and the third receiver, third rotatable clamping system and third stationary clamping system being configured to receive and clamp a fourth tube;
a first heater for heating a separation region of a first clamped tubing, a second heater for heating a separation region of a second clamped tubing, a third heater for heating a separation region of a third clamped tubing, and a fourth heater for heating a separation region of a fourth clamped tubing;
the respective rotatable and stationary clamping systems being relatively movable to separate the respective tubing clamped therebetween in the separation region;
the first and second receivers being relatively rotatable about their respective axis of rotation to place heated ends of separated first and second tubes in mechanical contact to form an integral bond with one another and the second and third receivers being relatively rotatable about the respective axis of rotation to place heated ends of separated third and fourth tubes in mechanical contact to form an integral bond with one another.

12. The system of claim 11 in which at least one of the first stationary and first rotatable clamping systems includes the first heater, at least one of the second stationary and second rotatable clamping systems includes the second heater, at least one of the third stationary and third rotatable clamping systems includes the third heater.

13. The system of claim 12 in which each heater comprises a high frequency voltage electrode.

14. The system of claim 11 in which the relatively rotatable and stationary clamping systems are also movable laterally to a respective axis of rotation.

15. The system of claim 11 in which each of the receivers comprises a disc having a disc surface on which respective tube or tubes are received and each disc is rotatable about an axis that is generally perpendicular to the surface of such disc.

16. The system of claim 15 in which the axes of rotation of the discs are substantially parallel.

17. The system of claim 15 in which the discs of the first receiver and the second receiver are substantially adjacent and the discs of the second receiver and the third receiver are substantially adjacent, whereby relative rotation between the discs of the first and second receivers will bring clamped ends of first and second tubes into contact and relative rotation between the discs of the second and third receivers will bring the clamped ends of third and fourth tubes into contact.

18. The system of claim 17 in which the disc of the second receiver is rotatable in one direction to bring a second tube into contact with a first tube and is rotatable in the opposite direction to bring a third tube into contact with a fourth tube.

19. The system of claim 18 including a rotary drive member and a linkage connecting the drive member to the receiver discs, the linkage being operable upon rotation of the drive member to shift the discs laterally between a position wherein the discs of the first and third receivers are spaced apart from the disc of the second receiver and a position wherein the first and third discs are more closely adjacent to the disc of the second receiver.

20. A system for making a plurality of sterile connections between a plurality of pairs of thermoplastic tubes, the system comprising:
a first receiver for receiving a first tube, a first clamping system including a tube heater associated with the first receiver,
a second receiver for receiving second and third tubes, a second clamping system including a tube heater associated with the second receiver;
a third receiver for receiving a fourth tube, a third clamping system including a tube heater associated with the third receiver;
the first receiver and second receiver being relatively movable to place clamped and heated ends of first and second tubes into contact to form an integral bond between them;
the second receiver and third receiver being relatively movable to place clamped and heated ends of third and fourth tubes into contact to form an integral bond between them; and
each clamping system including at least one clamp that is co-movable with the respective receiver with which is associated and at least one clamp that does not move with the respective receiver, whereby movement of the receiver exerts a tensile and/or a shear force on a tube clamped between such clamps of such respective system to sever such tube.

21. The system of claim 20 in which the first clamping system includes at least one clamp that is co-movable with the first receiver and at least one clamp that does not move with the first receiver, the second clamping system includes at least one clamp that is co-movable with the second receiver and at least two clamps that do not move with the second receiver, and the third clamping system includes at least one clamp that is co-movable with the third receiver and at least one clamp that does not move with the third receiver.

22. The system of claim 21 in which the at least one clamp of the second clamping system that is co-movable with the second receiver is also movable between a position for clamping a second tube and a position for clamping a third tube.

23. The system of claim 20 in which at least one of the first and second receivers and at least one of the second and third receivers is rotatable about an axis of rotation.

24. The system of claim 20 in which each of the receivers is rotatable about its own axis of rotation.

25. The system of claim 20 in which each of the receivers is configured to move a respective tube between a heating position and a bonding position.

26. The system of claim 20 in which each of the first, second and third receivers has a respective axis of rotation and each of the first and second receivers is relatively movable rotatably and laterally relative to their respective axis of rotation and the second and third receivers are relatively movable rotatably and laterally relative to their respective axis of rotation.

27. The system of claim 20 in which the tube heater of each clamping system comprises a heating element carried by at least one of the clamps of such system for heating a clamped tube.

28. The system of claim 20 in which the tube heater of each clamping system comprises at least one of the clamps of such system defining a high frequency voltage electrode.

\* \* \* \* \*